(12) United States Patent
Loganathan

(10) Patent No.: US 11,083,611 B2
(45) Date of Patent: Aug. 10, 2021

(54) IMPLANT DELIVERY SYSTEM

(71) Applicants: STRYKER CORPORATION, Kalamazoo, MI (US); STRYKER EUROPEAN HOLDINGS I, LLC, Kalamazoo, MI (US)

(72) Inventor: Siddharth Loganathan, Santa Clara, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/638,600

(22) PCT Filed: Aug. 22, 2018

(86) PCT No.: PCT/US2018/047582
§ 371 (c)(1),
(2) Date: Feb. 12, 2020

(87) PCT Pub. No.: WO2019/040652
PCT Pub. Date: Feb. 28, 2019

(65) Prior Publication Data
US 2020/0170817 A1 Jun. 4, 2020

Related U.S. Application Data

(60) Provisional application No. 62/549,233, filed on Aug. 23, 2017.

(51) Int. Cl.
*A61F 2/966* (2013.01)
(52) U.S. Cl.
CPC ...... *A61F 2/966* (2013.01); *A61F 2002/9665* (2013.01)
(58) Field of Classification Search
CPC .............. A61F 2/966; A61F 2002/9665; A61F 2250/0018; A61F 2002/9517; A61F 2250/0015; A61F 2/95; A61F 2/962
See application file for complete search history.

(56) References Cited

U.S. PATENT DOCUMENTS

2014/0200648 A1 7/2014 Newell et al.
2016/0100968 A1* 4/2016 Liang ............... A61F 2/962
623/1.12

FOREIGN PATENT DOCUMENTS

EP 2842525 A1 3/2015
EP 3 081 197 A1 10/2016
WO WO 2012/096687 A1 7/2012

OTHER PUBLICATIONS

PCT International Search Report for PCT/US2018/047582, Applicant: Stryker Coroporation, Form PCT/ISA/210 and 220, dated Nov. 21, 2018 (5 pages).

(Continued)

*Primary Examiner* — George J Ulsh
*Assistant Examiner* — Andrew P. Restaino
(74) *Attorney, Agent, or Firm* — Vista IP Law Group, LLP

(57) ABSTRACT

An implant delivery system comprises an elongate tubular member having a lumen, a tubular implant coaxially disposed within the lumen of the elongate tubular member, and a delivery assembly having a distal portion coaxially disposed within tubular implant. The delivery assembly comprises a delivery wire, an engaging bumper fixedly coupled to the delivery wire, a stopper bumper fixedly coupled to the delivery wire, and a floating element slidably coupled around the delivery wire and disposed between the bumpers, thereby limiting linear translation of the floating element therebetween. The floating element has an engaging portion configured to engage the engaging bumper when the delivery wire is axially translated relative to the elongate member in a first direction. The floating element is configured to radially expand outward to frictionally engage the implant when the engaging portion of the floating element engages the engaging bumper.

19 Claims, 8 Drawing Sheets

(56) References Cited

OTHER PUBLICATIONS

PCT Written Opinion of the International Search Authority for PCT/US2018/047582, Applicant: Stryker Coroporation, Form PCT/ISA/237, dated Nov. 21, 2018 (7 pages).

* cited by examiner

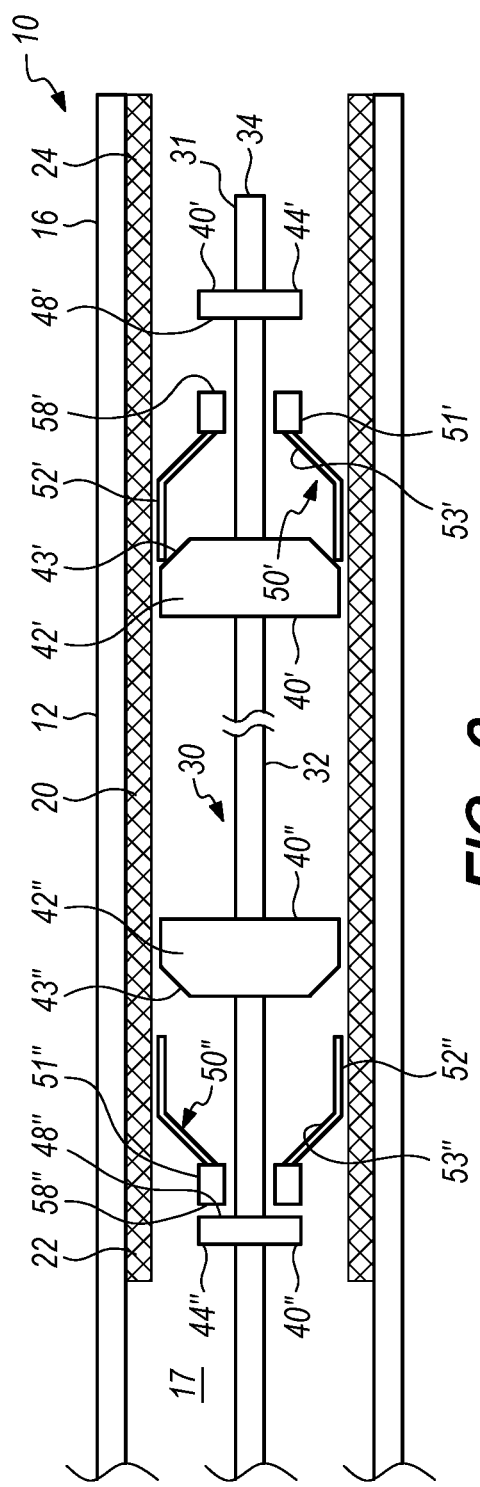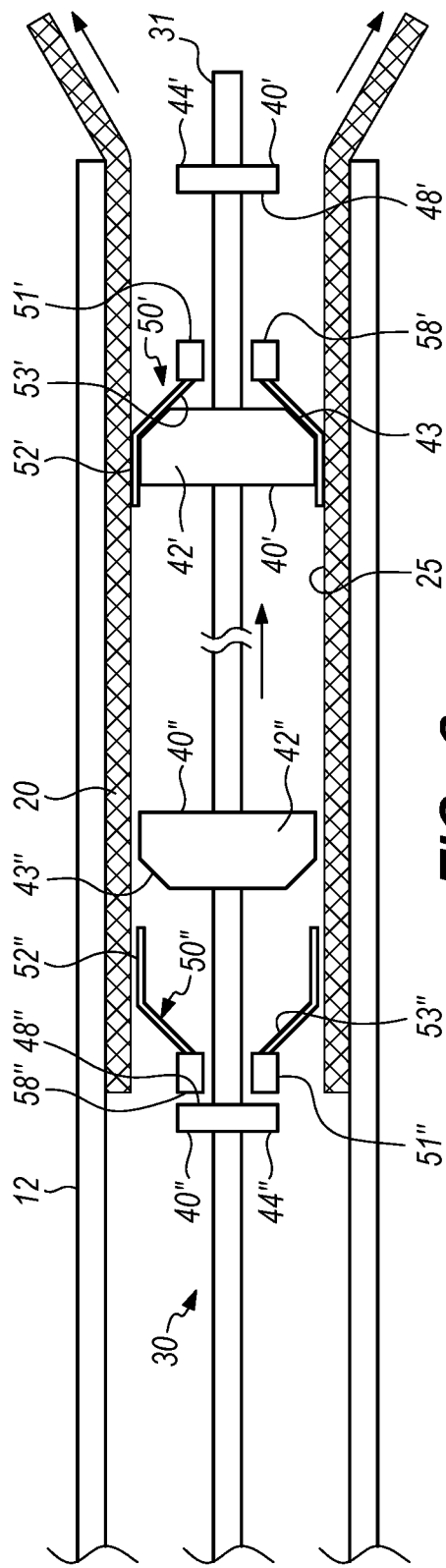

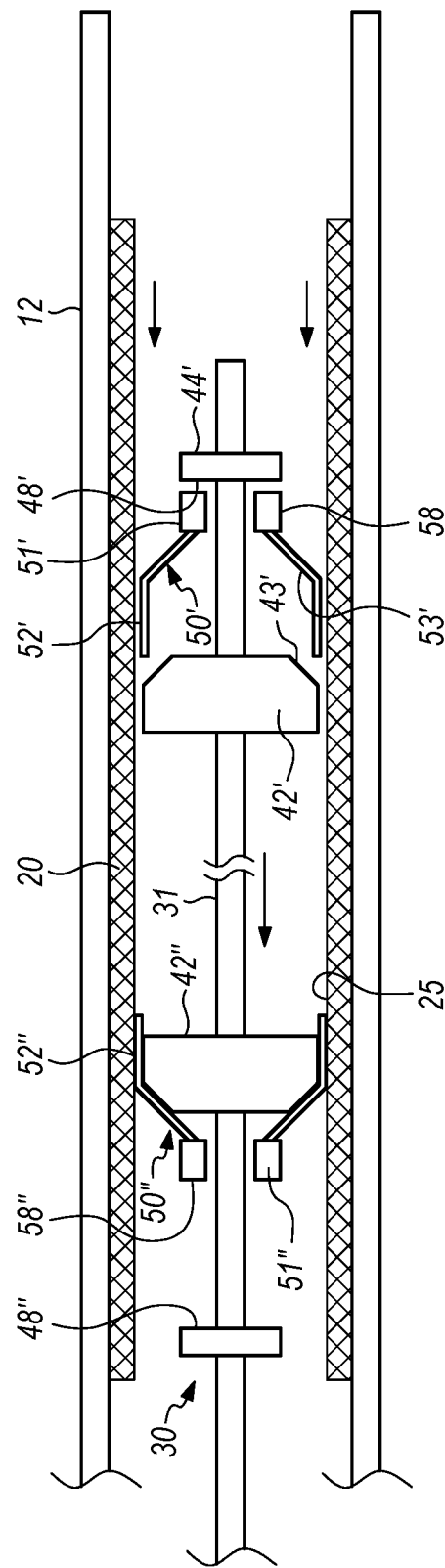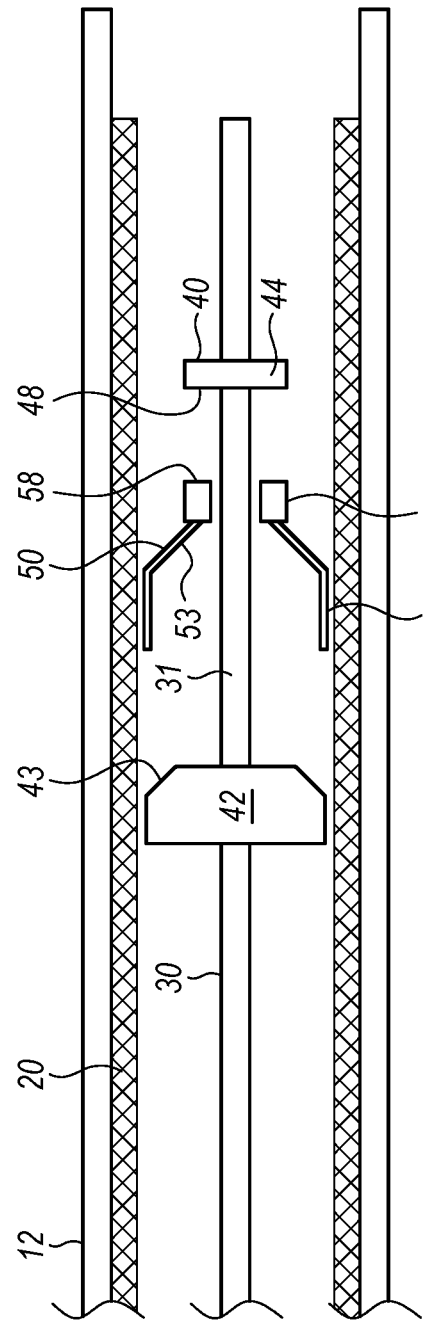

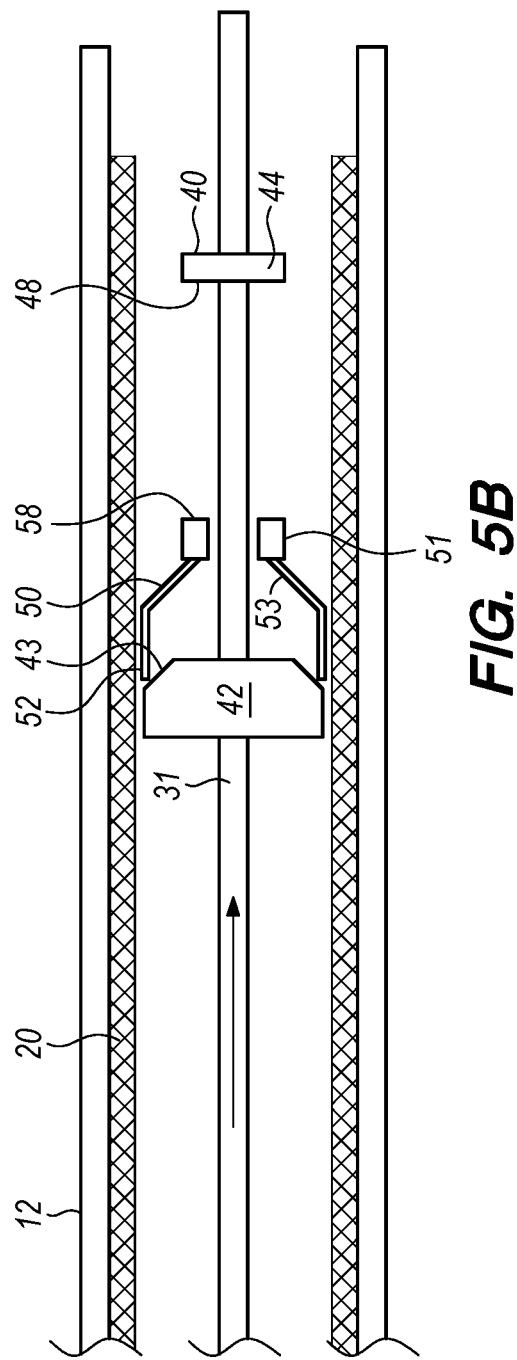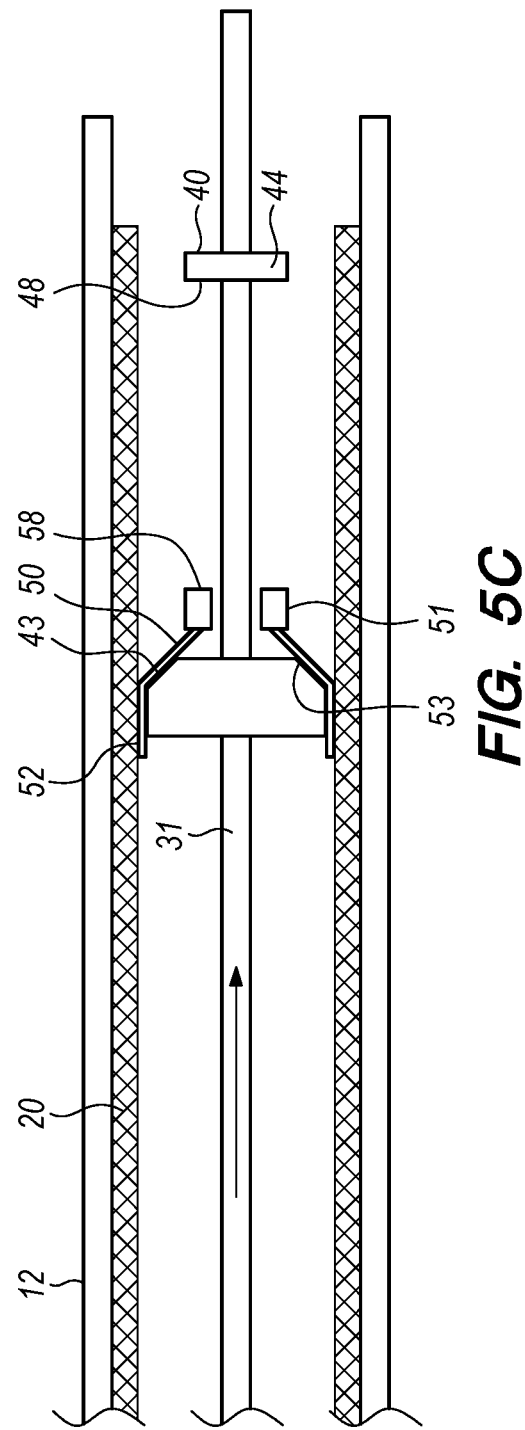

IMPLANT DELIVERY SYSTEM

RELATED APPLICATIONS DATA

The present application is a National Phase entry under 35 U.S.C § 371 of International Patent Application No. PCT/US2018/047582, having an international filing date of Aug. 22, 2018, which claims the benefit under 35 U.S.C. § 119 to U.S. Provisional Patent Application Ser. No. 62/549,233, filed Aug. 23, 2017, which is incorporated by reference in its entirety into the present application.

FIELD

The present disclosure relates generally to medical devices and intravascular medical procedures and, more particularly, to devices and methods for delivering an implant to a target site in a blood or other body vessel.

BACKGROUND

The use of intravascular medical devices has become an effective method for treating many types of vascular disease. In general, a suitable intravascular device is inserted into the vascular system of the patient and navigated through the vasculature to a desired target site. Using this method, virtually any target site in the patient's vascular system may be accessed, including the coronary, cerebral, and peripheral vasculature.

Medical implants, such as stents, stent grafts, flow-diverters, and vena cava filters, are often utilized in combination with a delivery device for placement at a desired location within the body. A medical implant, such as a stent, may be loaded into a stent delivery device and then introduced into the lumen of a body vessel in a configuration having a reduced diameter. Once delivered to a target location within the body, the stent may then be expanded to an enlarged configuration within the vessel to support and reinforce the vessel wall while maintaining the vessel in an open, unobstructed condition. The stent may be configured to be self-expanding, expanded by a stored potential radial force such as a balloon, or a combination of self-expanding and balloon expanded.

There is an ongoing need to provide alternative stent delivery devices that delivery medical implants into the vasculature of a patient.

SUMMARY

In accordance with a first embodiment of the disclosed inventions, an implant delivery system comprises an elongate tubular member having a lumen, a tubular implant coaxially disposed within the lumen of the elongate tubular member, and a delivery assembly having a distal portion coaxially disposed within tubular implant.

In accordance with one aspect of the disclosed inventions, the delivery assembly comprises a delivery wire, an engaging bumper fixedly coupled to the delivery wire, a stopper bumper fixedly coupled to the delivery wire, and a floating element slidably coupled around the delivery wire and disposed between the bumpers, thereby limiting linear translation of the floating element therebetween. The floating element has an engaging portion configured to engage the engaging bumper when the delivery wire is axially translated relative to the elongate member in a first direction, wherein the floating element is configured to radially expand (e.g., by flaring outward) to frictionally engage the implant when the engaging portion of the floating element engages the engaging bumper.

In one embodiment, the floating element comprises an annular portion slidably disposed around the delivery wire. The annular portion is configured to contact the stopper bumper when the delivery wire is axially translated relative to the elongate member in a second direction opposite to the first direction. The floating element is configured to maintain a radially unexpanded configuration in which the floating element does not frictionally engage the implant when the annular portion of the floating element contacts the stopper bumper. In various embodiments, the engaging portion of the floating element has an inner surface, and the engaging bumper has an outer surface that engages the inner surface of the floating element when the delivery wire is axially translated relative to the elongate member in the first direction. For example, the outer surface of the engaging bumper may taper inwards towards the engaging portion of the floating element.

In one embodiment, the annular portion of the floating element has an abutting surface and the stopper bumper has a corresponding abutting surface that abuts the abutting surface of the floating element when the delivery wire is axially translated relative to the elongate member in the second direction. In this case, the abutting surface of the stopper bumper may be substantially perpendicular to the second direction.

The engaging portion of the floating element may have one of a funnel-like, flower-like, and skirt-like configuration. For example, the engaging portion of the floating element may have a funnel-like configuration including an elastically compressible bent section disposed between two straight sections. The engaging portion of the floating element may have a flower-like configuration including a plurality of petal-like elements. The engaging portion of the floating element may have a flower-like configuration including a plurality of flaps.

In accordance with another embodiment of the disclosed inventions, a delivery assembly comprises a delivery wire, a first set of bumpers including a first engaging bumper and a first stopper bumper fixedly coupled to the delivery wire, a second set of bumpers including a second engaging bumper and a second stopper bumper fixedly coupled to the delivery wire, and a set of floating elements including a first floating element and a second floating element slidably coupled around the delivery wire.

The first floating element is disposed between the first engaging bumper and the first stopper bumper, thereby limiting linear translation of the first floating element therebetween. The first floating element has an engaging portion configured to engage the first engaging bumper when the delivery wire is axially translated in a first direction. The first floating element is configured to radially expand (e.g., by flaring outward) to frictionally engage the implant when the engaging portion of the first floating element engages the first engaging bumper.

The second floating element is disposed between the second engaging bumper and the second stopper bumper, thereby limiting linear translation of the second floating element therebetween. The second floating element has an engaging portion configured to engage the second engaging bumper when the delivery wire is axially translated relative to the elongate member in a second direction opposite the first direction. The second floating element is configured to radially expand (e.g., by flaring outward) to frictionally engage the implant when the engaging portion of the second floating element engages the second engaging bumper.

In one embodiment, the first floating element comprises an annular portion slidably disposed around the delivery wire. The annular portion is configured to contact the first stopper bumper when the delivery wire is axially translated relative to the elongate member in the second direction. The engaging portion of each of the first and second floating elements may have one of a funnel-like, flower-like, and skirt-like configuration. The first floating element is configured to maintain a non-radially expanded configuration in which the first floating element does not frictionally engage the implant when the annular portion of the first floating element contacts the first stopper bumper. The second floating element comprises an annular portion slidably disposed around the delivery wire. The annular portion is configured to contact the second stopper bumper when the delivery wire is axially translated relative to the elongate member in the first direction. The second floating element is configured to maintain a non-radially expanded configuration in which the second floating element does not frictionally engage the implant when the annular portion of the second floating element contacts the second stopper bumper.

In one such embodiment, the engaging portion of the first floating element has an inner surface and the first engaging bumper has a corresponding outer surface that tapers towards the engaging portion of the first floating element and engages the inner surface of the first floating element when the delivery wire is axially translated relative to the elongate member in the first direction, and the engaging portion of the second floating element has an inner surface and the second engaging bumper has a corresponding outer surface that tapers towards the engaging portion of the second floating element and that engages the inner surface of the second floating element when the delivery wire is axially translated relative to the elongate member in the second direction.

In one such embodiment, the annular portion of the first floating element has an abutting surface, and the first stopper bumper has an abutting surface perpendicular to the second direction that abuts the abutting surface of the first floating element when the delivery wire is axially translated relative to the elongate member in the second direction, and the annular portion of the second floating element has an abutting surface, and the second stopper bumper has an abutting surface perpendicular to the first direction that abuts the abutting surface of the second floating element when the delivery wire is axially translated relative to the elongate member in the first direction.

In accordance with a yet another embodiment, a method of operating the implant delivery system is provided, wherein the implant delivery system comprises an elongate tubular member having a lumen, a tubular implant coaxially disposed within the lumen of the elongate tubular member, and a delivery assembly having a distal portion coaxially disposed within tubular implant, and the delivery assembly comprises a delivery wire, a first engaging bumper fixedly coupled to the delivery wire, a first stopper bumper fixedly coupled to the delivery wire, and a first floating element slidably coupled around the delivery wire and disposed between the first bumpers, the method comprising axially translating the delivery wire relative to the elongate member in a first direction, while limiting linear translation of the first floating element between the first engaging bumper and the first stopper bumper, engaging the first engaging bumper with an engaging portion of the first floating element, such that the first floating element radially expands outward to frictionally engage the implant, and further axially translating the delivery wire relative to the elongate member in the first direction, thereby advancing the implant within the lumen of the elongate tubular member. The delivery wire may be further axially translated relative to the elongate member until the implant at least partially deploys out of the lumen of the elongate tubular member.

The deliver assembly may further comprise a second engaging bumper fixedly coupled to the delivery wire, a second stopper bumper fixedly coupled to the delivery wire, and a second floating element slidably coupled around the delivery wire and disposed between the second bumpers.

In this case, the method may further comprise axially translating the delivery wire relative to the elongate member in a second direction opposite to the first direction, while limiting linear translation of the second floating element between the second engaging bumper and the second stopper bumper, disengaging the first engaging bumper from the engaging portion of the first floating element, such that the first floating element radially contracts inwards to release the implant, engaging the second engaging bumper with an engaging portion of the second floating element, such that the second floating element radially expands outward to frictionally engage the implant, and continuing to axially translate the delivery wire relative to the elongate member in the second direction, thereby resheathing the implant within the lumen of the elongate tubular member.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments, without intention to be an exhaustive description or as a limitation on the scope of the disclosed inventions, which is defined only by the appended claims and their equivalents. In addition, the illustrated embodiments need not have all the aspects or advantages shown, and an aspect or an advantage described in conjunction with a particular embodiment is not necessarily limited to that embodiment and can be practiced in other embodiments, even if not so illustrated. In order to better appreciate how the above-recited and other advantages and objects are obtained, a more particular description of the disclosed inventions briefly described above will be rendered by reference to specific embodiments thereof, which are illustrated in the accompanying drawings, in which:

FIG. 2 is a cross-sectional view of the distal portion of the implant delivery system constructed according to one embodiment of the disclosed inventions;

FIG. 3 is a cross-sectional view of the implant delivery system of FIG. 2, showing advancement of the delivery assembly and engaging the implant for delivery;

FIG. 4 is a cross-sectional view of the implant delivery system of FIG. 2, showing withdrawal of the delivery assembly and engaging the implant for re-sheathing;

FIGS. 5A-5D are cross-sectional views an alternative embodiment of the implant delivery system of FIG. 2, particularly showing the process of engaging the implant;

DETAILED DESCRIPTION OF THE ILLUSTRATED EMBODIMENTS

Figure 1:
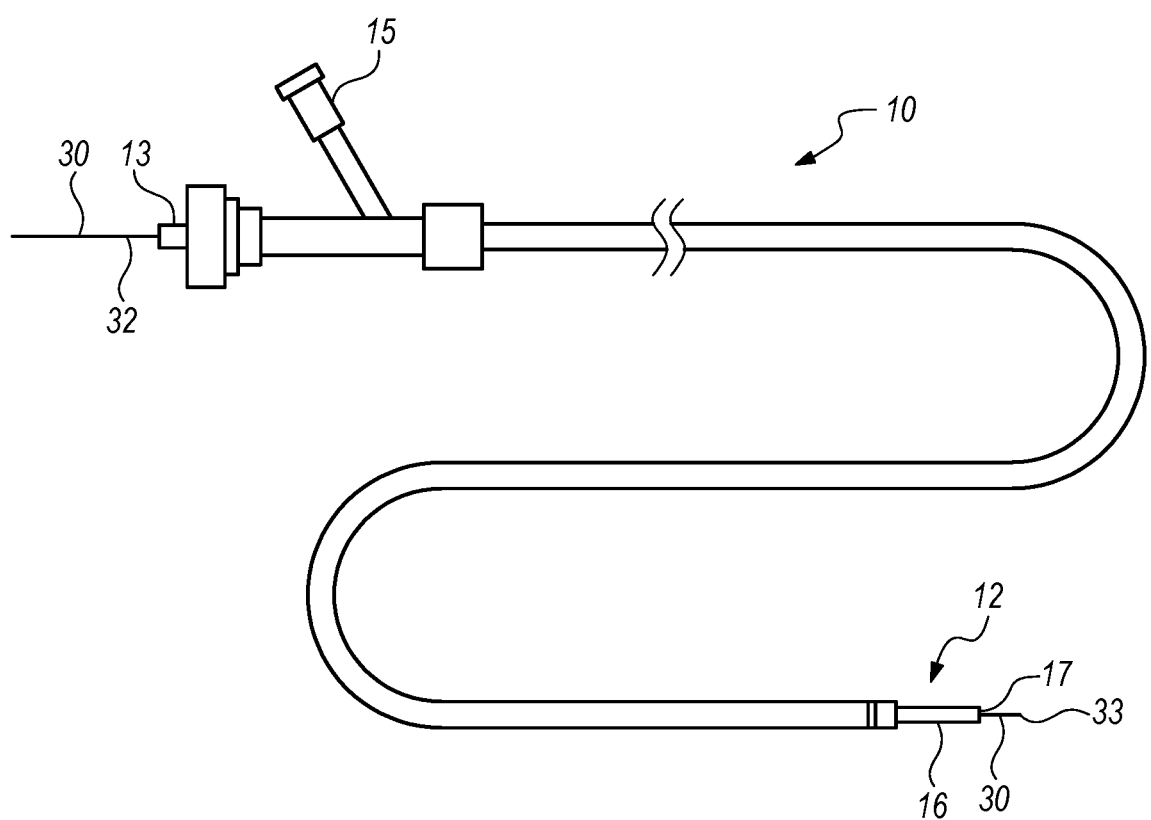
FIG. 1 is a side view of an implant delivery system constructed according to one embodiment of the disclosed inventions, with a distal region of the system shown in an inset.

Referring first to FIG. 1, one embodiment of an implant delivery system 10 constructed in accordance with one embodiment of the disclosed inventions will be described. The implant delivery system 10 generally comprises an elongate tubular member 12, a tubular implant 20 (not shown in FIG. 1), and a delivery assembly 30.

The elongate member 12 has a tubular configuration, and can, e.g., take the form of a sheath, catheter, micro-catheter or the like. The elongate member 12 has a proximal portion 13, a distal portion 16, and a lumen 17 extending through the elongate member 12 between the proximal portion 13 and the distal portion 16. The proximal section 13 of the elongate member 12 remains outside of the patient and accessible to the operator when the implant delivery system 10 is in use, while the distal portion 16 of the elongate member 12 is sized and dimensioned to reach remote locations of a vasculature and is configured to deliver the implant 20 to a target location in a patient's body, such as an occlusion in a blood vessel, in a blood vessel adjacent to an aneurysm neck, a bifurcated blood vessel, or the like. The implant delivery system 10 has at least one fluid port 15 in fluid communication with the elongate member 12, which is used to introduce fluids into the elongate member 12. The implant 20 and delivery assembly 30 are disposed in the lumen 17 of the elongate member 12 of the implant delivery system 10, as better appreciated in FIG. 2.

The implant 20, such a stent or a flow diverter, includes a tubular resilient member having a proximal portion 22, a distal portion 24, and defining an inner lumen 26 extending therebetween (FIG. 2). The implant 20 has a delivery configuration when disposed within the lumen 17 of the elongate member 12 and/or is radially constrained by the elongate member 12. The implant 20 is biased to expand radially outwards into a deployed configuration in which the implant 20 is expanded when deployed out of the elongate member 12. The implant 20 may be constructed from a variety of materials such as stainless steel, elgiloy, nickel, titanium, nitinol, shape memory polymers, or combinations thereof. The implant 20 may also be formed in a variety of manners as well. For example, the implant 20 may be formed by etching or cutting a pattern from a tube or sheet of stent material; a sheet of stent material may be cut or etched according to a desired stent pattern whereupon the sheet may be rolled or otherwise formed into the desired substantially tubular, bifurcated or other shape. For the implant 20, one or more wires or ribbons of stent material may be woven, braided or otherwise formed into a desired shape and pattern. The implant 20 may include further components that are welded, bonded or otherwise engaged to one another. The implant 20 may include a non-porous, non-permeable biocompatible material, cover or the like, when the implant 20 is used as a blood flow diverter.

The implant delivery system 10 may be used in an "over-the-wire" configuration, wherein the elongate member 12 is introduced into the patient over a guidewire which has been previously introduced, and the elongate member 12 extends over the entire length of the guidewire (not shown). Alternatively, the implant delivery system 10 may be used in a "rapid-exchange" configuration, where a guidewire extends through only a distal portion of the implant delivery system 10 from a guidewire port (not shown). In other alternative embodiments, the implant delivery system 10 may be introduced into the patient after a guidewire had been withdrawn leaving a sheath or access catheter distal portion at the target site for the assembly 10 to navigate through the vasculature of the patient within the sheath or access catheter.

The implant delivery system 10 may include one or more, or a plurality of regions along its length having different configurations and/or characteristics. For example, the distal portion 16 of the elongate member 12 may have an outer diameter less than the outer diameter of the proximal portion 13 to reduce the profile of the distal portion 16 and facilitate navigation in tortuous vasculature (FIG. 1). Furthermore, the distal portion 16 may be more flexible than the proximal portion 13. Generally, the proximal portion 13 may be formed from material that is stiffer than the distal portion 16 of the elongate member 12, so that the proximal portion 13 has sufficient pushability to advance through the patient's vascular system, while the distal portion 16 may be formed of a more flexible material so that the distal portion 16 may remain flexible and track more easily over a guidewire to access remote locations in tortuous regions of the vasculature. The elongate member 12 may be composed of suitable polymeric materials, metals and/or alloys, such as polyethylene, stainless steel or other suitable biocompatible materials or combinations thereof. In some instances, the proximal portion 13 may include a reinforcement layer, such a braided layer or coiled layer to enhance the pushability of the elongate member 12. The elongate member 12 may include a transition region between the proximal portion 13 and the distal portion 16.

Referring further to FIG. 2, the implant 20 is coaxially disposed within the distal portion 16 of elongate member 12, and the delivery assembly 30 is coaxially disposed and axially movable relative to the elongate member 12 and the implant 20. The delivery assembly 30 is configured to engage the implant 20 when the system 30 is axially translated relative to the elongate member 12 for delivery of the implant 20 into a target site of a patient. The interface between the delivery assembly 30 and the implant 20 will be described in further detail below.

The delivery assembly 30 comprises a delivery wire 31 having a proximal region 32 and a distal region 33 (FIG. 1). The delivery wire 31 may be made of a conventional guidewire, torqueable cable tube, a hypotube or the like. In either case, there are numerous materials that can be used for the delivery wire 31 to achieve the desired properties that are commonly associated with medical devices. Some examples can include metals, metal alloys, polymers, metal-polymer composites, and the like, or any other suitable material. For example, the delivery wire 31 may include nickel-titanium alloy, stainless steel, a composite of nickel-titanium alloy and stainless steel. In some cases, the delivery wire 31 can be made of the same material along its length, or in some embodiments, can include portions or sections made of different materials. In some embodiments, the material used to construct the delivery wire 31 is chosen to impart varying flexibility and stiffness characteristics to different portions of the delivery wire 31. For example, the proximal region and the distal region 33 of the delivery wire 31 may be formed of different materials, such as materials having different moduli of elasticity, resulting in a difference in flexibility. For example, the proximal region 32 can be formed of stainless steel, and the distal region 33 can be formed of a nickel-titanium alloy. However, any suitable material or combination of material may be used for the delivery wire 31, as desired.

The delivery wire 31 may further include a distal shapeable or pre-shaped atraumatic end 34 (FIG. 2), which may aid the advancement of the delivery wire 31. In some embodiments, the distal end 34 may include a coil placed over a portion of a distal end of the delivery wire 31 (not shown) or, alternatively, may include a material melted down and placed over a portion of the distal end 34 of the delivery wire 31. In some embodiments, the distal end 34 may include a radiopaque material to aid in visualization. Additionally, the distal end 34 of the delivery wire 31 may be floppy and steerable using pull wires (not shown) to facilitate tracking of the delivery assembly 30 through a vessel to reach a target site. Although not illustrated, it is contemplated that the distal end 34 of the delivery wire 31 may include one or more tapered sections, as desired.

The delivery wire 31 may optionally include one or more bands (not shown) in the distal region 33 of the delivery wire 31. The bands may be formed integrally into the delivery wire 31, or they may be separately formed from the delivery wire 31 and attached thereto. In some embodiments, the bands may be disposed on the delivery wire 31. The bands may have a diameter greater than the diameter of the surrounding the delivery wire 31. Bands may be formed of any suitable material, such as metals, metal alloys, polymers, metal-polymer composites, and the like, or any other suitable material, as well as any radiopaque material, as desired. Alternatively, it is contemplated that the delivery wire 31 may include one or more recesses instead of providing bands, if desired.

Significantly, the delivery assembly 30 comprises at least one set of bumpers 40 fixedly coupled to the delivery wire 31, and a floating element 50 slidably coupled to the delivery wire 31. In the embodiment of FIG. 2, two sets of bumpers 40 (a first set of distal bumpers 40' and a second set of proximal bumpers 40") are disposed at the distal portion 32 of the delivery wire 31, with each set having a respective floating element 50'/50" therebetween. In particular, the distal bumpers 40' include a distal engaging bumper 42' and a distal stopper bumper 44', with a distal floating element 50' therebetween, and the proximal bumpers 40" include a proximal engaging bumper 42" and a proximal stopper bumper 44", with a proximal floating element 50" therebetween. The engaging bumpers 42/42'/42" and the stopper bumpers 44/44'/44" are configured to limit translation of the respective floating elements 50/50'/50" therebetween. Additionally, the engaging bumpers 42/42"/42' are configured to interface with the respective floating elements 50/50'/50" to engage (i.e., frictionally engage) the implant 20 for delivery to a target site (FIGS. 3, 5A-D) and/or re-sheathing the implant 20 into the elongate member 12 (FIG. 4).

Each floating element 50/50'/50" has an annular portion 51/51'/51", such as a collar, ring or the like, and engaging portion 52/52'/52" having an inner surface 53/53'/53" configured to interface with an outer surface 43/43'/43" of the engaging bumper 42/42'/42" when the delivery assembly 30 is actuated, which is described in further detail below.

Between the distal set of bumpers 40', the engaging portion 52' of the distal floating element 50' is proximately disposed to the annular portion 51' of the distal floating element 50', such that the interface between the distal engaging bumper 42' and engaging portion 52' of the distal floating element 50' is configured to engage the implant 20 when the delivery wire 31 is advanced or translated in the distal direction for delivery of the implant 20 into the target site of the patient (FIG. 3).

In contrast, between the proximal set of bumpers 40", the engaging portion 52" of the proximal floating element 50" is distally disposed to the annular portion 51 of the proximal floating element 50", such that the interface between the proximal engaging bumper 42" and engaging portion 52" of the proximal floating element 50" is configured to engage the implant 20 when the delivery wire 31 is withdrawn or translated in the proximal direction for re-sheathing of the implant 20 into the elongate member 12 (FIG. 4).

As shown in FIG. 3, the delivery assembly 30 is actuated by advancing (i.e., distally translating, axially moving) the delivery wire 31 relative to the elongate member 12. When the delivery wire 31 is advanced relative to the elongate member 12, the distal engaging bumper 42' interfaces with the engaging portion 52' of the distal floating element 50', wherein the outer surface 43' of the engaging bumper 42' contacts the inner surface 53' of the engaging portion 52', so that the engaging portion 52' of the distal floating element 50' is disposed between the distal engaging bumper 42' and the implant 20. The interface between the distal engaging bumper 42' and the engaging portion 52' of the distal floating element 50' exerts a radially outward force on an interior surface 25 of the implant 20. This radially outward force is sufficient to contact and frictionally engage the implant 20 so as to advance and deliver the implant 20 to a target site when the delivery wire 31 advances relative to the elongate member 12. Furthermore, when the delivery wire 31 is advanced relative to the elongate member 12, the proximal stopper bumper 44" contacts the annular portion 51" of the proximal floating element 50", advancing and distally pushing the proximal floating element 50" along with the advancement of the delivery wire 31. As shown in FIG. 3, the proximal floating element 50" does not frictionally engage the implant 20 during advancement of the delivery wire 31.

As shown in FIG. 4, the delivery assembly 30 is actuated by withdrawing (i.e., proximately translating, axially moving) the delivery wire 31 relative to the elongate member 12. When the delivery wire 31 is withdrawn relative to the elongate member 12, the proximal engaging bumper 42" interfaces with the engaging portion 52" of the proximal floating element 50", wherein the outer surface 43 of the engaging bumper 42" contacts the inner surface 53" of the engaging portion 52", so that the engaging portion 52" of the proximal floating element 50" is disposed between the proximal engaging bumper 42" and the implant 20. The interface between the proximal engaging bumper 42" and the engaging portion 52 of the proximal floating element 50" exerts a radially outward force on the interior surface 25 of the implant 20. This radially outward force is sufficient to frictionally engage the implant 20 so as to withdraw and re-sheath the implant 20 when the delivery wire 31 is withdrawn relative to the elongate member 12. Furthermore, when the delivery wire 31 is withdrawn relative to the elongate member 12, the distal stopper bumper 44' contacts the annular portion 51' of the distal floating element 50', withdrawing and proximally pushing the distal floating element 50' along with the withdrawal of the delivery wire 31. As shown in FIG. 4, the distal floating element 50' does not frictionally engage the implant 20 during withdrawal of the delivery wire 31.

Thus, as can be appreciated, the delivery assembly 30 of the implant delivery system 10 comprises a bi-directional actuation. Particularly, as shown in FIG. 3, when the delivery wire 31 is axially translated relative to the elongate member 12 in a first direction (i.e., advanced in a distal direction), the implant 20 is engaged by the interface between the distal engaging bumper 42' and the engaging portion 52' of the distal floating element 50', while the proximal floating element 50" does not engage the implant 20. Conversely, as shown in FIG. 4, when the delivery wire 31 is axially translated relative to the elongate member 12 in a second direction, opposite to the first direction (i.e., withdrawn in a proximal direction), the implant 20 is engaged by the interface between the proximal engaging bumper 42" and the engaging portion 52" of the proximal floating element 50", while the distal floating element 50' does not engage the implant 20. The bi-directional delivery assembly 30 provides the operator of the implant delivery system 10 with the advantage of being able to both deliver or re-sheath the implant 20 by either advancing or withdrawing the delivery wire 31 relative to the elongate member 12.

While the embodiment depicted in FIGS. 2-4 comprises a delivery assembly 30 having two sets of bumpers 40' and 40", each having a respective floating member 50'/50", an alternative embodiment of the delivery assembly 30 may have more than two sets of bumpers 40 and floating members 50. Still another embodiment of the delivery assembly 30 may comprise only one set of bumpers 40 with only one floating member 50.

Figure 5D:
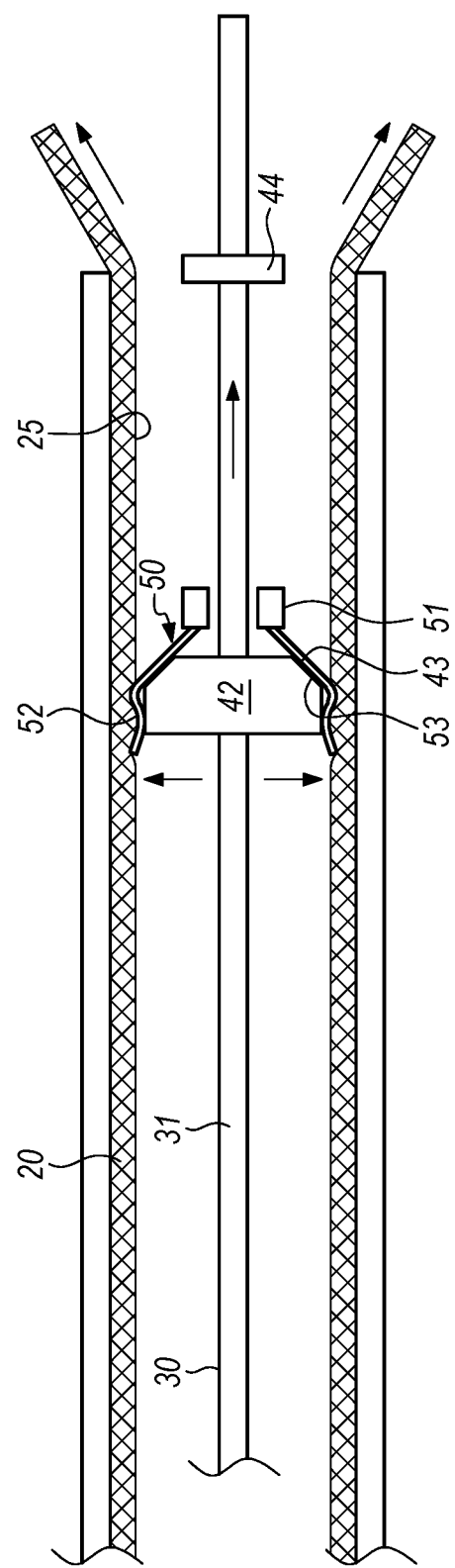

For example, as shown in FIGS. 5A-D, the delivery assembly 30 comprises one set of bumpers 40 and one floating element 50 for delivery of the implant 20 into the target site. The delivery assembly 30 is actuated by advancing (i.e., distally translating, axially moving) the delivery wire 31 relative to the elongate member 12. When the delivery wire 31 is advanced relative to the elongate member 12, the engaging bumper 42 approaches the floating element 50 (FIGS. 5A-B), and as the delivery wire 31 further advances, the outer surface 43 of the engaging bumper 42 interfaces with (i.e., contacts) the inner surface 53 the engaging portion 52 of the floating element 50 (FIG. 5C), so that the engaging portion 52 of the floating element 50 is disposed between the engaging bumper 42 and the implant 20, frictionally engaging the implant 20 (FIG. 5D). As best seen in FIG. 5D, the interface between the engaging bumper 42 and the engaging portion 52 of the floating element 50 exerts a radially outward force (shown by arrows in FIG. 5D) on an interior surface 25 of the implant 20. This radially outward force is sufficient to frictionally engage implant 20 so as to advance the implant within the elongate member 12, and deliver the implant 20 to a target site when the delivery wire 31 advances relative to the elongate member 12.

In the embodiments of FIGS. 2-5D, each floating element 50/50'/50" is configured to radially expand outward (e.g., by flaring outward) to frictionally engage the implant 20 when the engaging portion 52/52'/52" of the floating element 50/50'/50" engages the respective engaging bumper 42/42'/42". In some embodiments, the engaging portion 52/52'/52" of the floating elements 50/50'/50" is dimensioned and sized to partially enter or occupy openings/cells in the implant 20 (FIG. 5D), thereby allowing further engagement and/or frictional forces between the delivery assembly 30 and the implant 20. This design assists the axial displacement of the implant 20 relative to the elongate element 12, further facilitating delivery or re-sheathing of the implant 20.

In these embodiments and as best seen in FIG. 5C, the outer surface 43 of the engaging bumper 42 engages the inner surface 53 of the floating element 50 to radially expand the floating element 50 outwardly and frictionally contact and/or engage the implant 20 for translation relative to the elongate element 12. To facilitate engagement between the engaging portion 52 of the floating element 50 and the respective engaging bumper 42, and the consequential outward radial expansion of the floating element 52, in the illustrated embodiments, the outer surface 43 of the engaging bumper 42 tapers inwards towards the engaging portion 52 of the respective floating element 52. While the engaging bumpers 42/42'/42" depicted in FIGS. 2-5D comprise a disk-shape having a tapered annular portion, the engaging bumpers 42/42'/42" may include a variety of configurations having any cross-section, such as irregular shapes, as long as at least one cross-sectional dimension is suitable to interface with the inner surface 53/53'/53" of the engaging portion 52/52'/52" of the floating element 50/50'/50" and frictionally engage the implant 20, as previously described.

In the embodiments of FIGS. 2-5D, each floating element 50/50'/50" is configured to not radially expand outwardly (e.g., by not flaring outwardly), such that there is no frictional engagement with the implant 20 when the floating element 50/50'/50" engages the respective stopper bumper 44/44'/44". In these embodiments, the annular portion 51/51'/51" of each floating element 50/50'/50" has an abutting surface 58/58'/58", and the respective stopper bumper 44/44'/44" has an abutting surface 48/48'/48" that abuts the abutting surface 58/58'/58" of the floating element 50/50'/50" to axially displace the floating element 50/50'/50" relative to the implant 20. To facilitate engagement between the floating element 50/50'/50" and the respective stopper bumper 44/44'/44", and the consequential axial displacement of the floating element 50/50'/50" relative to the implant 20, the abutting surface 58/58'/58" of the annular portion 51/51'/51" of each floating element 50/50'/50" and the abutting surface 48/48'/48" of the stopper bumper 44/44'/44" are both perpendicular to the axial movement of the floating element 50/50'/50". While the stopper bumpers 44/44'/44" depicted in FIGS. 2-5D comprise a disk-shape configuration, and the stopper bumpers 44/44'/44" may comprise a variety of configuration, including irregular shapes, as long as at the stopper bumpers 44/44'/44" axially translates the floating element 50/50'/50" over the delivery wire 31 relative to the implant 20, as previously described.

As depicted in FIGS. 2-5D, the engaging bumpers 42/42'/42" and the stopper bumpers 44/44'/44" have respective cross-sectional dimensions that are smaller than the inner diameter of the implant 20 in the delivery configuration, when the implant 20 is disposed within the lumen 17 of the elongate member 12. In the embodiments of FIGS. 2-4, the engaging bumpers 42/42'/42" have a cross-sectional dimension larger than the stopper bumpers 44/44'/44". In the embodiments of FIGS. 5A-D, the engaging bumper 42/42'/42" has a cross-sectional dimension substantially similar to the stopper bumper 44/44'/44". It should be appreciated that variations of the relative dimensions of the engaging bumpers 42/42'/42" and the stopper bumpers 44/44'/44" may be suitable in some embodiments.

In the embodiments depicted in FIGS. 2-8B, the engaging portion 52/52'/52" extending from the annular portion 51/51'/51" of the floating element 50/50'/50" is composed of suitable biocompatible material configured to be elastically compressible, for instance, stainless steel, elgiloy, nickel, titanium, nitinol, shape memory polymers, or combinations thereof. There are numerous materials that can be used for floating element 50/50'/50" to achieve the desired properties for the interface of the engaging portion 52/52'/52" with the engaging bumper 42/42'/42" of the delivery assembly 30. Some examples can include metals, metal alloys, polymers, metal-polymer composites, and the like, or any other suitable material. Examples of suitable metals and metal alloys can include stainless steel, nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, or the like; or other suitable metals, or combinations or alloys thereof. Examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, or mixtures, blends or combinations thereof. Further, the engaging portion 52/52'/52" of the floating device 50/50'/50" may be formed by etching or cutting a pattern from a tube or sheet, or may be formed by one or more wires or ribbons of suitable materials woven, braided or otherwise formed into a desired shape and pattern. Further, the engaging bumpers 42/42'/42" and/or the stopper bumpers 44/44'/44" may be radiopaque, in which case they function as markers to facilitate determination of delivery wire 31 position.

Figure 6:
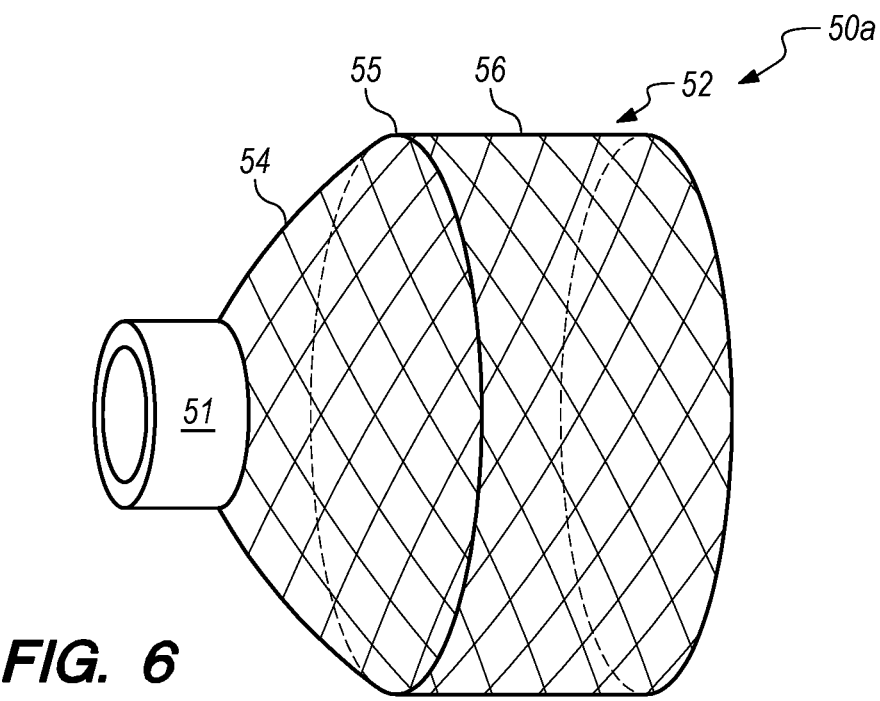
FIG. 6 is a perspective view of one embodiment of a floating element that can be used in the implant delivery system of FIG. 1 or FIG. 5.
Figure 7:
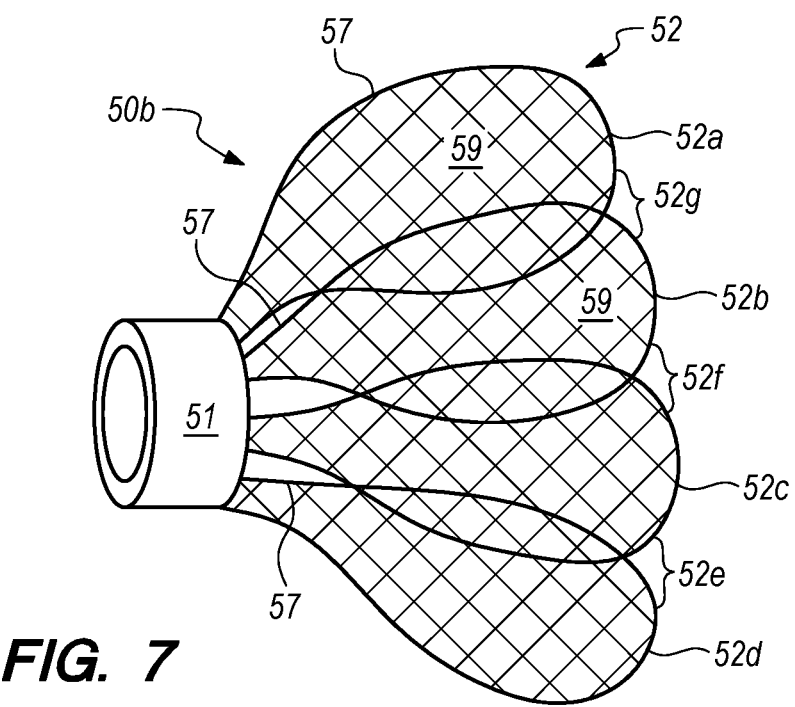
FIG. 7 is a perspective view of another embodiment of a floating element that can be used in the implant delivery system of FIG. 1 or FIG. 5.

The engaging portion 52/52'/52" of each floating element 50/50'/50" may have one of a funnel-like, flower-like, and skirt-like configuration. Various embodiments of the floating element 50/50'/50" are depicted in FIGS. 6-8. For example, with reference to FIG. 6, a floating element 50a comprises a funnel-like configuration, where the engaging portion 52 includes a bent section 55 disposed between two straight sections 54 and 56. The bent section 55 is configured to be elastically compressible, for instance, by heat-setting a stainless steel or shape memory alloy (e.g., nitinol). The engaging portion 52 extends from the annular portion 51 of the floating element 50a, and is formed of suitable filaments or ribbons woven, braided or formed into a mesh. It should be appreciated that the engaging portion 52 of the floating element 50a may be formed of a solid material, such as a liner, cover, or the like. Alternatively, the liner or cover may be permeable, porous, or includes apertures or perforations (not shown).

With reference to FIG. 7, a floating element 50b comprises a flower-like configuration, where the engaging portion 52 includes a plurality of petal-like elements 52a-g extending from the annular portion 51. The petal-like elements 52a-g may be formed by looped filaments 57 coupled to the annular portion 51, where each of the looped filament 57 may have a respective braided cover 59 disposed therein. It should be appreciated that the petal-like elements 52a-g of the engaging portion 52 of the floating element 50b may be formed by the looped filaments 57 without any braided cover disposed therein, or the petal-like elements 52a-g may be formed of a solid material, such as a liner, cover, or the like. Alternatively, the liner or cover may be permeable, porous, or includes apertures or perforations (not shown). The petal-like elements 52a-g may overlap with respective adjacently disposed petal-like elements, as shown in FIG. 7.

Figure 8A:
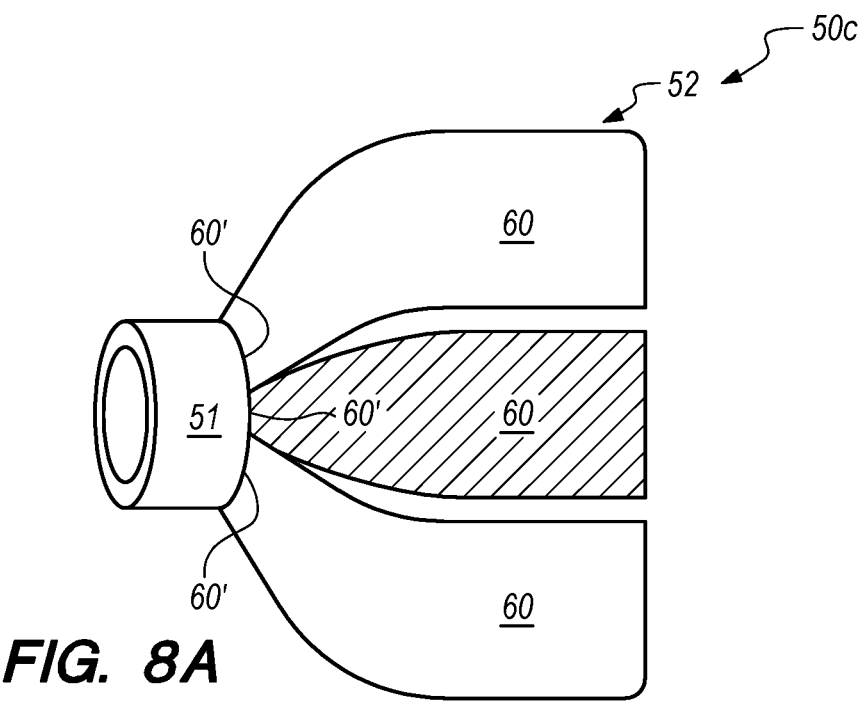
FIGS. 8A-8B are perspective views of embodiments of a floating element that can be used in the implant delivery system of FIG. 1 or FIG. 5.
Figure 8B:
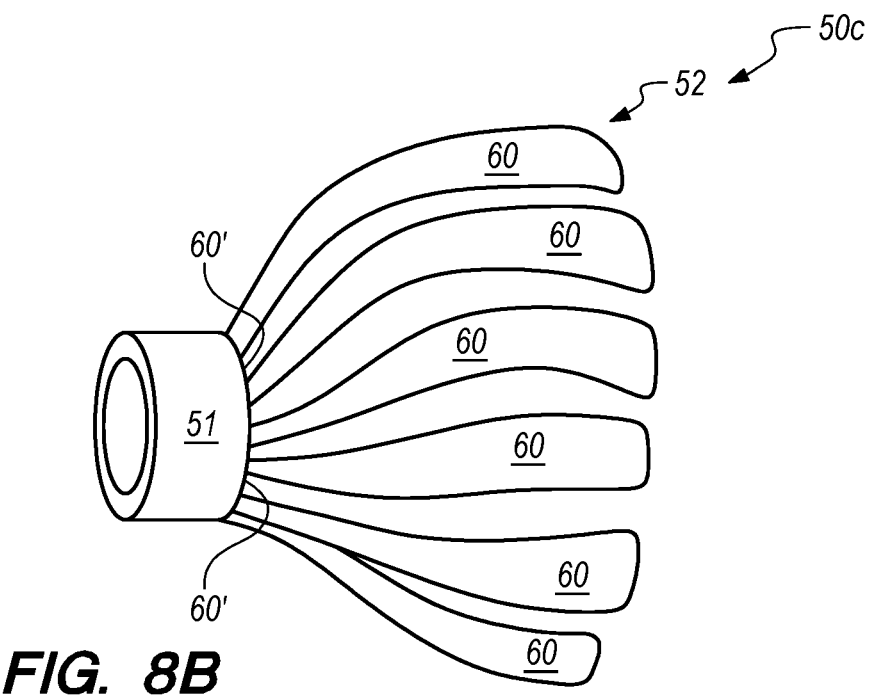

With reference to FIGS. 8A-8B, the engaging portion 52 of a floating element 50c comprises a plurality of flaps 60 having respective ends 60' coupled to or extending from the annular portion 51. It should be appreciated that the plurality of flaps 160 of the engaging portion 52 of the floating element 50c may be permeable, porous, or includes apertures or perforations (not shown).

Figure 9:
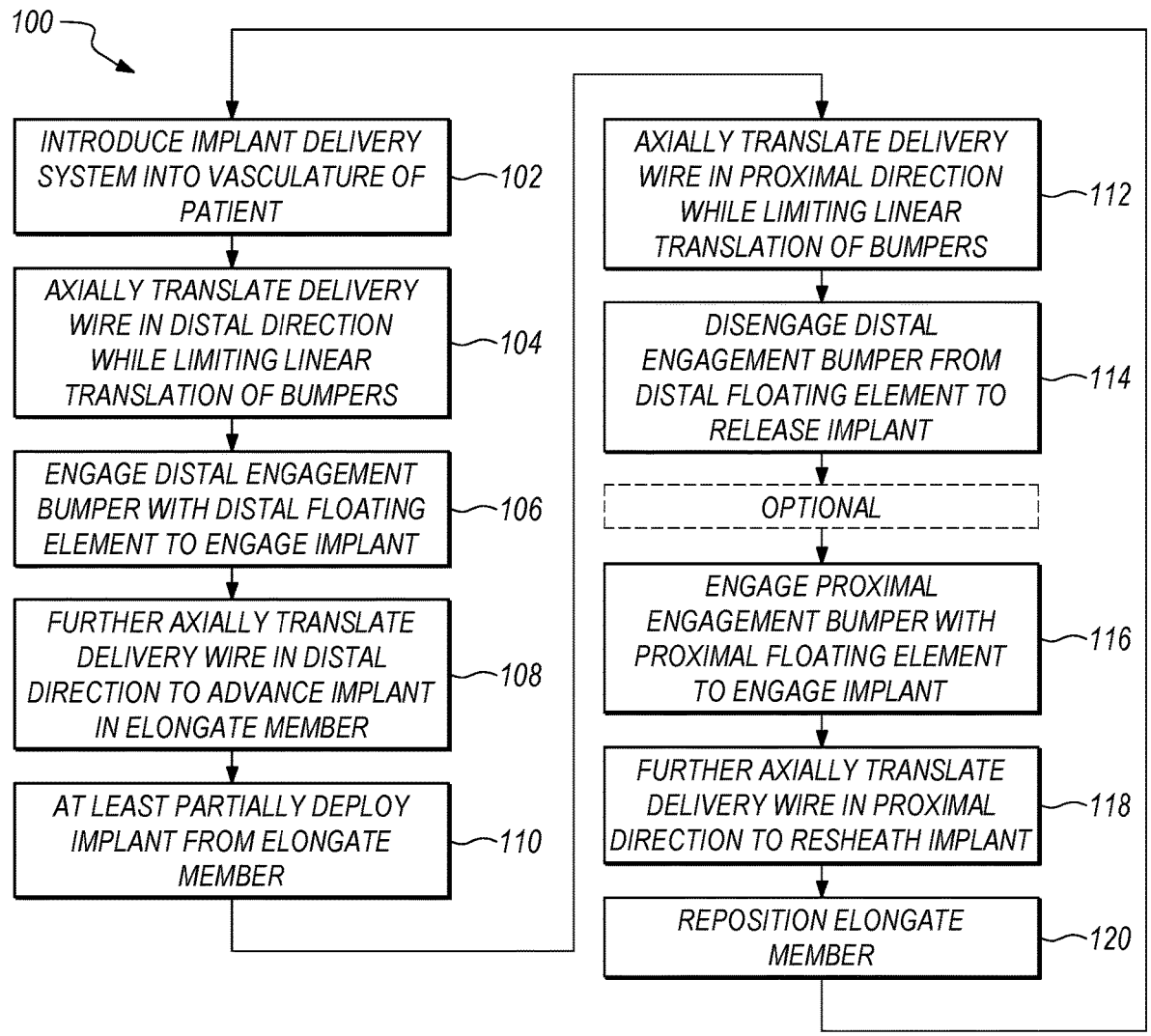
FIG. 9 is a flow diagram illustrating one method of operating the implant delivery system of FIG. 2.

Having described the function and structure of the implant delivery system 10, one method 100 of using the implant delivery system 10 illustrated in FIG. 2 will now be discussed in FIG. 9. First, the implant delivery system 10 is introduced into the vasculature of a patient in a conventional manner, such that the distal portion 16 of the elongate member 12 is adjacent a target site within the vasculature of the patient (step 102). Next, the delivery wire 31 is axially translated in the distal direction relative to the elongated member 12, while limiting linear translation of the first (in this case the distal) floating element 50' between the first (in this case, the distal) engaging bumper 42' and the first (in this case, the distal) stopper bumper 44' (step 104). Next, the distal engaging bumper 42' is engaged with the engaging portion 52' of the distal floating element 50', such that the distal floating element 50' radially expands outward to frictionally engage the implant 20 (step 106). Then, the delivery wire 31 is further axially translated relative to the elongate member 12 in the distal direction, thereby advancing the implant 20 within the lumen 17 of the elongate member 12 (step 108). The delivery wire 31 is axially translated relative to the elongate member 12 until the implant 20 at least partially deploys out of the lumen 17 of the elongate member 12 (step 110).

If the implant 20 is only partially deployed, the implant 20 may be resheathed back into the elongate member 20 if it is decided that the deployment site of the implant 20 is not inaccurate. In particular, the delivery wire 31 is axially translated relative to the elongate member 12 in the proximal direction, while limiting linear translation of the second (in this case the proximal) floating element 50" between the second (in this case, the proximal) engaging bumper 42" and the second (in this case, the proximal) stopper bumper 44" (step 112). The distal engaging bumper 42' is disengaged from the engaging portion 52' of the distal floating element 50', such that the distal floating element 50' radially contracts inwards to release the implant 20 (step 114). Next, the proximal engaging bumper 42" is engaged with the engaging portion 52 of the proximal floating element 50", such that the proximal floating element 50" radially expands outward to frictionally engage the implant 20 (step 116). Optionally, the delivery wire 31 is further axially translated relative to the elongate member 12 in the proximal direction, thereby resheathing the implant 20 within the lumen 17 of the elongate member 12 (step 118). The distal portion 16 of the elongate member 12 can be repositioned (step 120), and steps 102-110, and if necessary steps 112-118, can be repeated.

Although particular embodiments of the disclosed inventions have been shown and described herein, it will be understood by those skilled in the art that they are not intended to limit the disclosed inventions, and it will be obvious to those skilled in the art that various changes and modifications may be made (e.g., the dimensions of various parts). The specification and drawings are, accordingly, to be regarded in an illustrative rather than restrictive sense.

The invention claimed is:

1. An implant delivery system, comprising:
an elongate tubular member having a lumen;
a tubular implant coaxially disposed within the lumen of the elongate tubular member; and
a delivery assembly having a distal portion coaxially disposed within tubular implant, the delivery assembly comprising:
a delivery wire;
an engaging bumper fixedly coupled to the delivery wire;
a stopper bumper fixedly coupled to the delivery wire; and
a floating element slidably coupled around the delivery wire and disposed between the bumpers, the floating element comprising an engaging portion configured to engage the engaging bumper when the delivery wire is axially translated relative to the elongate tubular member in a first direction, wherein the floating element is configured to radially expand and frictionally engage the implant when the engaging portion of the floating element engages the engaging bumper.

2. The implant delivery system of claim 1, the floating element further comprising an annular portion slidably disposed around the delivery wire, the annular portion configured to contact the stopper bumper when the delivery wire is axially translated relative to the elongate tubular member in a second direction opposite to the first direction, and wherein the floating element is configured to maintain a non-radially expanded configuration in which the floating element does not frictionally engage the implant when the annular portion of the floating element contacts the stopper bumper.

3. The implant delivery system of claim 2, wherein the annular portion of the floating element has an abutting surface, and the stopper bumper has an abutting surface that abuts the abutting surface of the floating element when the delivery wire is axially translated relative to the elongate member in the second direction.

4. The implant delivery system of claim 3, wherein the abutting surface of the stopper bumper is perpendicular to the second direction.

5. The implant delivery system of claim 1, wherein the floating element radially expands by flaring outward when the engaging portion of the floating element engages the engaging bumper.

6. The implant delivery system of claim 1, wherein the engaging portion of the floating element has an inner surface, and the engaging bumper has an outer surface that contacts the inner surface of the floating element when the delivery wire is axially translated relative to the elongate member in the first direction.

7. The implant delivery system of claim 6, wherein the outer surface of the engaging bumper tapers inwards towards the engaging portion of the floating element.

8. The implant delivery system of claim 1, wherein the engaging portion of the floating element has one of a funnel-like, flower-like, and skirt-like configuration.

9. The implant delivery system of claim 8, wherein the engaging portion of the floating element has a funnel-like configuration including an elastically compressible bent section disposed between two straight sections.

10. The implant delivery system of claim 8, wherein the engaging portion of the floating element has a flower-like configuration including a plurality of petal-like elements.

11. The implant delivery system of claim 8, wherein the engaging portion of the floating element has a flower-like configuration including a plurality of flaps.

12. A method of operating the implant delivery system of claim 1, the method comprising:
axially translating the delivery wire relative to the elongate member in the first direction, while limiting linear translation of the floating element between the engaging bumper and the stopper bumper;
engaging the engaging bumper with the engaging portion of the floating element, such that the floating element radially expands outward to frictionally engage the implant; and
further axially translating the delivery wire relative to the elongate member in the first direction, thereby advancing the implant within the lumen of the elongate tubular member.

13. The method of claim 12, wherein the delivery wire is further axially translated relative to the elongate member until the implant at least partially deploys out of the lumen of the elongate tubular member.

14. An implant delivery system, comprising:
an elongate tubular member having a lumen;
a tubular implant coaxially disposed within the lumen of the elongate tubular member; and
a delivery assembly having a distal portion coaxially disposed within tubular implant, the delivery assembly comprising:
a delivery wire;
a first set of bumpers including a first engaging bumper and a first stopper bumper fixedly coupled to the delivery wire;
a second set of bumpers including a second engaging bumper and a second stopper bumper fixedly coupled to the delivery wire; and
a set of floating elements including a first floating element and a second floating element slidably coupled around the delivery wire;
wherein the first floating element is disposed between the first engaging bumper and the first stopper bumper thereby limiting linear translation of the first floating element therebetween, the first floating element comprising an engaging portion configured to engage the first engaging bumper when the delivery wire is axially translated relative to the elongate member in a first direction, wherein the first floating element is configured to radially expand and frictionally engage the implant when the engaging portion of the first floating element engages the first engaging bumper; and
wherein the second floating element is disposed between the second engaging bumper and the second stopper bumper, thereby limiting linear translation of the second floating element therebetween, the second floating element comprising an engaging portion configured to engage the second engaging bumper when the delivery wire is axially translated relative to the elongate member in a second direction opposite the first direction, wherein the second floating element is configured to radially expand and frictionally engage the implant when the engaging portion of the second floating element engages the second engaging bumper.

15. The implant delivery system of claim 14,
the first floating element further comprising an annular portion slidably disposed around the delivery wire, the annular portion configured to contact the first stopper bumper when the delivery wire is axially translated relative to the elongate member in the second direction, wherein the first floating element is configured to maintain a non-radially expanded configuration in which the first floating element does not frictionally engage the implant when the annular portion of the first floating element contacts the first stopper bumper; and
the second floating element further comprising an annular portion slidably disposed around the delivery wire, the annular portion configured to contact the second stopper bumper when the delivery wire is axially translated relative to the elongate member in the first direction, wherein the second floating element is configured to maintain a non-radially expanded configuration in which the second floating element does not frictionally engage the implant when the annular portion of the second floating element contacts the second stopper bumper.

16. The implant delivery system of claim 15,
wherein the annular portion of the first floating element has an abutting surface, and the first stopper bumper has an abutting surface perpendicular to the second direction that abuts the abutting surface of the first floating element when the delivery wire is axially translated relative to the elongate member in the second direction; and
wherein the annular portion of the second floating element has an abutting surface and the second stopper bumper has an abutting surface perpendicular to the first direction that abuts the abutting surface of the second floating element when the delivery wire is axially translated relative to the elongate member in the first direction.

17. The implant delivery system of claim 14, wherein each of the first floating element and second floating element radially expands by flaring outward.

18. The implant delivery system of claim 14,
wherein the engaging portion of the first floating element has an inner surface, and the first engaging bumper has an outer surface that tapers towards the engaging portion of the first floating element and engages the inner surface of the first floating element when the delivery wire is axially translated relative to the elongate member in the first direction; and
wherein the engaging portion of the second floating element has an inner surface and the second engaging bumper has an outer surface that tapers towards the engaging portion of the second floating element and that engages the inner surface of the second floating element when the delivery wire is axially translated relative to the elongate member in the second direction.

19. The implant delivery system of claim 14, wherein the respective engaging portions of the first and second floating elements have one of a funnel-like, flower-like, and skirt-like configuration.

* * * * *